United States Patent [19]

Emberger et al.

[11] Patent Number: 5,145,703
[45] Date of Patent: Sep. 8, 1992

[54] THIO-ALKANONES, PROCESS FOR THEIR PREPARATION AND THEIR USE

[75] Inventors: Roland Emberger; Matthias Günter; Rudolf Hopp; Manfred Köpsel; Walter Kuhn, all of Holzminden; Peter Werkhoff, Hoexter, all of Fed. Rep. of Germany

[73] Assignee: Haarmann & Reimer, Holzminden, Fed. Rep. of Germany

[21] Appl. No.: 701,545

[22] Filed: May 16, 1991

[30] Foreign Application Priority Data

May 23, 1990 [DE] Fed. Rep. of Germany ....... 4016536

[51] Int. Cl.$^5$ .................. A23L 2/26; A61K 31/38
[52] U.S. Cl. .................. 426/535; 426/536; 514/445; 514/473; 549/62; 549/66; 549/475; 549/479
[58] Field of Search ............ 549/62, 66, 475, 479; 426/535, 536; 514/445, 473

[56] References Cited

U.S. PATENT DOCUMENTS

| | | | |
|---|---|---|---|
| 3,933,863 | 1/1976 | Evers et al. | 260/347.2 |
| 3,958,029 | 5/1976 | Evers et al. | 260/347.2 |
| 3,961,093 | 6/1976 | Evers et al. | 260/347.2 |
| 4,119,737 | 10/1978 | van den Bosch et al. | 426/535 |
| 4,380,655 | 4/1983 | van den Bosch et al. | 549/472 |
| 4,477,678 | 10/1984 | van den Bosch et al. | 549/62 |
| 4,555,359 | 11/1985 | Bruns et al. | 568/374 |

OTHER PUBLICATIONS

Chemical Abstracts, vol. 115, No. 1, Jul. 8, 1991, Columbus, Ohio Abstract No. 7192R pp. 715–716.

*Primary Examiner*—C. Warren Ivy
*Assistant Examiner*—Ba K. Trinh
*Attorney, Agent, or Firm*—Sprung Horn Kramer & Woods

[57] ABSTRACT

The invention relates to new thio-alkanones of the formula

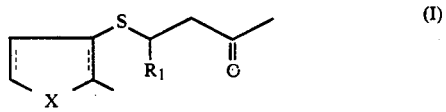

in which
X represents an oxygen or sulphur atom,
$R_1$ represents hydrogen or a $C_1$–$C_2$-alkyl group and the broken lines represent a single bond or no bond,
to a process for their preparation and their use as flavorings.

1 Claim, No Drawings

THIO-ALKANONES, PROCESS FOR THEIR PREPARATION AND THEIR USE

The invention relates to new thio-alkanones, to a process for their preparation and to their use as flavourings.

New thio-alkanones of the formula

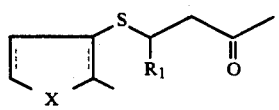
(I)

have now been found in which
X represents an oxygen or sulphur atom,
$R_1$ represents hydrogen or a $C_1$–$C_2$-alkyl group and the broken lines represent a single bond or no bond.

It has additionally been found that these thio-alkanones of the formula (I) have useful organoleptic properties.

The invention therefore relates to the new thioalkanones of the formula (I) and their use as flavourings.

The thioalkanones according to the invention are obtained by addition of thiols of the formula

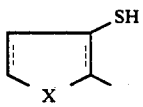
(II)

in which X and the broken lines have the meaning indicated under formula (I), to ketones of the formula

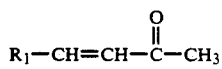
(III)

in which $R_1$ has the meaning indicated under formula (I).

The invention therefore also relates to a process for the preparation of thioalkanones of the formula (I); the process is characterised in that thiols of the formula (II) are added to alkanones of the formula (III).

The addition can be carried out at temperatures from 0° C. to 50° C., preferably at room temperature, in an inert solvent such as alcohols, preferably ethanol, or ethers, preferably tetrahydrofuran.

The thiols of the formula (II) required as starting compounds are described in DE-OS (German Published Specification) 2.458,609 and the ketones of the formula (III) are described, for example, in DE-PS (German Patent Specification) 877,606 and DE-OS (German Published Specification) 3,212,326.

The compounds of the formula (I) according to the invention are useful flavourings; they are distinguished by very low taste threshold values. Thus, a test panel of 20 testers in a triangle test using 4-(2-methyl-3-furyl-thio)-pentan-2-one in 0.5% strength aqueous sodium chloride solution even found a significant difference between the blank sample and the sodium chloride solution only containing 1 ppb of 4-(2-methyl-3-furyl-thio)-pentan-2-one. For 4-(2-methyl-3-tetrahydrofuryl-thio)-pentan-2-one, a test panel of 6 specially trained testers found a significant difference between the 0.5% strength aqueous sodium chloride solution and the 0.5% strength sodium chloride solution containing 1.5 ppb of 4-(2-methyl-3-tetrahydrofuryl-thio)-pentan-2-one.

The taste descriptions for the individual compounds of the formula (I) according to the invention for their use in 0.5% strength aqueous sodium chloride solution read:

4-(2-methyl-3-furyl-thio)-pentan-2-one:
  in an addition of 15 ppb: stock, meaty, processed flavour type meat
  in an addition of 150 ppb: fullness, meaty, beef stock, slight roast meat character in the background
4-(2-methyl-3-tetrahydrofuryl-thio)-pentan-2-one: in an addition of 15 ppb: cooked meat, meat stock, slight roast meat character
4-(2-methyl-3-thienylthio)-pentan-2-one: in an addition of 15 ppb: mushroomy, herby
4-(2-methyl-3-thienyl-thio)-butan-2-one: in an addition of 15 ppb: fatty, slightly roast meat, slightly peanut, meat With their specific taste towards meat, the compounds of the formula (I) according to the invention act in a taste-reinforcing and -rounding-off manner in meat flavour compositions. However, in other flavour compositions, for example nut flavourings, the compounds according to the invention also cause a rounding-off of the flavour and an increase in the fullness of taste.

The flavour compositions prepared using the compounds according to the invention can be employed in the entire foodstuff and luxury goods sector, and also in animal feed. They are suitable, in particular, for fatty materials, baking goods, extruded products, ready-to-serve meals, meats and sausage products, soups, sauces, vegetable preserves and all types of industrially prepared animal feed.

The new thio-alkanones according to the invention are used in amounts of 5 ppt to 1%, preferably 100 ppt to 100 ppm, relative to the ready-to-consume foodstuff.

The percentage data used in the examples are percentages by weight.

EXAMPLE 1

10 g of 2-methylfuryl-3-thiol and 15 g of 3-penten-2-one were dissolved in 100 ml of ethanol. The solution was allowed to stand at room temperature for 48 hours. The solvent was then distilled off in vacuo at 50° C. The residue (18 g) was purified by preparative high pressure liquid chromatography (HPLC). 9 g of 4-(2-methyl-3-furanyl-thio)-pentan-2-one (degree of purity 96%) were obtained. IR, NMR and mass spectra of the compound agree with that of the structure indicated.

When using 2-methyltetrahydrofuryl-3-thiol or 2-methyl-thienyl-3-thiol instead of 2-methylfuryl-3-thiol and 3-buten-2-one instead of 3-penten-2-one, 4-(2-methyl-3-tetrahydrofuryl-thio)-pentan-2-one, 4-(2-methyl-3-thienyl-thio)-pentan-2-one and 4-(2-methyl-3-thienyl-thio)-butan-2-one were obtained.

EXAMPLE 2

A meat flavour composition was prepared by mixing the following constituents in the parts by weight indicated:

| | |
|---|---|
| 50:50 mixture of Na inosinate and Na guanilate | 1 |
| Monosodium glutamate | 19 |
| Lactic acid, spray-dried | 30 |
| Vegetable protein hydrolysate (Type RFB from FIS) | 350 |
| Sweet whey powder | 100 |

| | |
|---|---:|
| -continued | |
| Table salt | 500 |
| | 1,000 |

A 1% aqueous solution of this composition was used as a control sample.

If 1.5 ppm of 4-(2-methyl-3-furylthio)-pentan-2-one was added to the control sample, the flavour of the aqueous solution was described by a test group as distinctly fuller and meatier towards roast beef in comparison to the control sample.

On adding 1.5 ppm of 4-(2-methyl-tetrahydrofurylthio)-pentan-2-one, the flavour was described as substantially fuller with pronounced meaty character and a slight roast (crackling) character.

We claim:

1. A process of enhancing the flavor of foodstuffs for humans and animals by addition of an effective flavor enhancing amount of a thio-alkanone of the formula

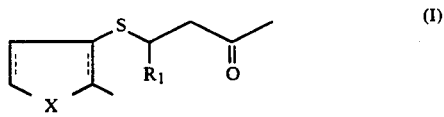

in which
  X represents an oxygen or sulphur atom,
  $R_1$ represents hydrogen or a $C_1$–$C_2$-alkyl group and the broken lines represent a single bond or no bond.

* * * * *